(12) United States Patent
Cao et al.

(10) Patent No.: US 10,874,402 B2
(45) Date of Patent: Dec. 29, 2020

(54) DETACHABLE RF ENERGIZED OCCLUSIVE DEVICE

(71) Applicant: BOSTON SCIENTIFIC SCIMED, INC., Maple Grove, MN (US)

(72) Inventors: Hong Cao, Maple Grove, MN (US); Kent David Harrison, Maple Grove, MN (US); Timothy A. Ostroot, Cokato, MN (US); Matthew Ryan DeWitt, Georgetown, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 16/155,454

(22) Filed: Oct. 9, 2018

(65) Prior Publication Data
US 2019/0105055 A1    Apr. 11, 2019

Related U.S. Application Data

(60) Provisional application No. 62/570,173, filed on Oct. 10, 2017.

(51) Int. Cl.
*A61B 17/12* (2006.01)
*A61B 17/00* (2006.01)
(Continued)

(52) U.S. Cl.
CPC .... *A61B 17/12113* (2013.01); *A61B 17/0057* (2013.01); *A61B 17/12031* (2013.01);
(Continued)

(58) Field of Classification Search
CPC .. A61B 2017/1205; A61B 2017/12054; A61B 2017/1209; A61B 17/12109; A61B 17/12113
See application file for complete search history.

(56) References Cited

U.S. PATENT DOCUMENTS

| 5,117,839 A | 6/1992 | Dance |
| 5,122,136 A | 6/1992 | Guglielmi et al. |

(Continued)

FOREIGN PATENT DOCUMENTS

| EP | 2777542 A2 | 9/2014 |
| EP | 2777545 A2 | 9/2014 |

(Continued)

OTHER PUBLICATIONS

International Search Report & Written Opinion dated Jun. 15, 2018 for International Application No. PCT/US2018/021978.

(Continued)

*Primary Examiner* — Wade Miles
(74) *Attorney, Agent, or Firm* — Seager, Tufte & Wickhem LLP

(57) ABSTRACT

An occlusive medical device system may include a microcatheter, an elongate shaft, an occlusive medical device, wherein a release wire is configured to releasably attach the medical device to the distal end of the shaft at a release mechanism, and an RF generator. In a first electrical state current is not flowing and in a second electrical state current is flowing to the medical device. The shaft is slidable between a first position wherein the medical device is disposed within the microcatheter, a second position wherein at least a portion of the medical device is disposed outside of the microcatheter and the release mechanism is disposed within the microcatheter, and a third position wherein the release mechanism is disposed outside of the microcatheter. The medical device system is configured to be in the second electrical state when the elongate shaft is in the second position.

19 Claims, 7 Drawing Sheets

(51) Int. Cl.
*A61F 2/01* (2006.01)
*A61B 18/14* (2006.01)
*A61B 18/08* (2006.01)

(52) U.S. Cl.
CPC .. *A61B 17/12109* (2013.01); *A61B 17/12122* (2013.01); *A61B 17/12145* (2013.01); *A61B 18/082* (2013.01); *A61B 18/1492* (2013.01); *A61F 2/013* (2013.01); *A61B 2017/12054* (2013.01); *A61B 2018/1435* (2013.01); *A61B 2018/1475* (2013.01); *A61B 2018/1495* (2013.01)

(56) References Cited

U.S. PATENT DOCUMENTS

| | | | |
|---|---|---|---|
| 5,234,437 | A | 8/1993 | Sepetka |
| 5,250,071 | A | 10/1993 | Palermo |
| 5,282,478 | A | 2/1994 | Fleischhaker, Jr. et al. |
| 5,304,195 | A | 4/1994 | Twyford, Jr. et al. |
| 5,312,415 | A | 5/1994 | Palermo |
| 5,546,958 | A | 8/1996 | Thorud et al. |
| 5,743,905 | A | 4/1998 | Eder et al. |
| 5,851,206 | A * | 12/1998 | Guglielmi ........ A61B 17/12022 606/28 |
| 6,019,757 | A * | 2/2000 | Scheldrup ........ A61B 17/12109 606/49 |
| RE37,117 | E | 3/2001 | Palermo |
| 6,270,495 | B1 | 8/2001 | Palermo |
| 6,277,125 | B1 | 8/2001 | Barry et al. |
| 6,478,773 | B1 * | 11/2002 | Gandhi ................ A61B 17/12 604/113 |
| 6,491,646 | B1 | 12/2002 | Blackledge |
| 6,656,173 | B1 | 12/2003 | Palermo |
| 6,953,473 | B2 | 10/2005 | Porter |
| 7,044,134 | B2 | 5/2006 | Khairkhahan et al. |
| 7,708,755 | B2 | 5/2010 | Davis et al. |
| 7,815,661 | B2 | 10/2010 | Mirizzi et al. |
| 7,896,899 | B2 | 3/2011 | Patterson et al. |
| 8,142,456 | B2 | 3/2012 | Rosqueta |
| 8,216,229 | B2 | 7/2012 | Elliott |
| 8,236,042 | B2 | 8/2012 | Berez et al. |
| 8,333,786 | B2 | 12/2012 | Mirizzi et al. |
| 8,333,796 | B2 | 12/2012 | Tompkins et al. |
| 8,641,777 | B2 | 2/2014 | Strauss et al. |
| 8,679,111 | B2 | 3/2014 | Oyola et al. |
| 8,696,701 | B2 | 4/2014 | Becking et al. |
| 8,747,597 | B2 | 6/2014 | Rosqueta et al. |
| 8,795,313 | B2 | 8/2014 | Liang et al. |
| 8,801,746 | B1 | 8/2014 | Kreidler et al. |
| 8,911,487 | B2 | 12/2014 | Bennett et al. |
| 9,017,350 | B2 | 4/2015 | Karabey et al. |
| 9,017,361 | B2 | 4/2015 | Karabey et al. |
| 9,060,773 | B2 | 6/2015 | Nguyen et al. |
| 9,119,948 | B2 | 9/2015 | Lee et al. |
| 9,186,151 | B2 | 11/2015 | Tompkins et al. |
| 9,198,670 | B2 | 12/2015 | Hewitt et al. |
| 9,301,827 | B2 | 4/2016 | Strauss et al. |
| 9,307,999 | B2 | 4/2016 | Li et al. |
| 9,414,819 | B2 | 8/2016 | Fitz et al. |
| 9,468,442 | B2 | 10/2016 | Huynh et al. |
| 9,498,226 | B2 | 11/2016 | Cage et al. |
| 9,549,740 | B2 | 1/2017 | Rees |
| 9,554,805 | B2 | 1/2017 | Tompkins et al. |
| 9,561,125 | B2 | 2/2017 | Bowman et al. |
| 2002/0120297 | A1 | 8/2002 | Shadduck |
| 2002/0169473 | A1 * | 11/2002 | Sepetka ................ A61L 31/145 606/200 |
| 2003/0050635 | A1 | 3/2003 | Truckai et al. |
| 2006/0036281 | A1 | 2/2006 | Patterson et al. |
| 2006/0206140 | A1 | 9/2006 | Shaolian et al. |
| 2006/0212055 | A1 | 9/2006 | Karabey et al. |
| 2006/0229669 | A1 | 10/2006 | Mirizzi et al. |
| 2006/0282159 | A1 | 12/2006 | Taheri |
| 2007/0135826 | A1 | 6/2007 | Zaver et al. |
| 2007/0156123 | A1 * | 7/2007 | Moll .................. A61B 17/0057 606/1 |
| 2007/0270903 | A1 | 11/2007 | Davis et al. |
| 2007/0282373 | A1 | 12/2007 | Ashby et al. |
| 2008/0004692 | A1 | 1/2008 | Henson et al. |
| 2008/0086196 | A1 | 4/2008 | Truckai et al. |
| 2008/0109059 | A1 | 5/2008 | Gordon et al. |
| 2008/0119891 | A1 | 5/2008 | Miles et al. |
| 2008/0300616 | A1 | 12/2008 | Que et al. |
| 2009/0043331 | A1 | 2/2009 | Buiser et al. |
| 2009/0062838 | A1 | 3/2009 | Brumleve et al. |
| 2009/0062845 | A1 | 3/2009 | Tekulve |
| 2009/0163934 | A1 | 6/2009 | Raschdorf, Jr. et al. |
| 2009/0177261 | A1 | 7/2009 | Teoh et al. |
| 2009/0270978 | A1 | 10/2009 | Virkler et al. |
| 2009/0287291 | A1 | 11/2009 | Becking et al. |
| 2009/0287294 | A1 | 11/2009 | Rosqueta et al. |
| 2010/0106178 | A1 | 4/2010 | Obermiller et al. |
| 2010/0121350 | A1 | 5/2010 | Mirigian |
| 2010/0174269 | A1 | 7/2010 | Tompkins et al. |
| 2010/0234872 | A1 * | 9/2010 | Guo .................. A61B 17/12022 606/191 |
| 2011/0166588 | A1 | 7/2011 | Connor et al. |
| 2011/0184454 | A1 | 7/2011 | Barry et al. |
| 2011/0202085 | A1 | 8/2011 | Loganathan et al. |
| 2011/0238147 | A1 | 9/2011 | Bennett et al. |
| 2011/0265943 | A1 | 11/2011 | Rosqueta et al. |
| 2011/0301686 | A1 * | 12/2011 | Bowman ............ A61M 25/0021 623/1.11 |
| 2011/0319926 | A1 | 12/2011 | Becking et al. |
| 2012/0041470 | A1 * | 2/2012 | Shrivastava ........ A61B 17/1219 606/200 |
| 2012/0046687 | A1 | 2/2012 | Trommeter et al. |
| 2012/0203322 | A1 | 8/2012 | Eells |
| 2012/0283812 | A1 | 11/2012 | Lagodzki |
| 2012/0316598 | A1 | 12/2012 | Becking et al. |
| 2012/0330341 | A1 | 12/2012 | Becking et al. |
| 2012/0330347 | A1 | 12/2012 | Becking et al. |
| 2012/0330348 | A1 | 12/2012 | Strauss et al. |
| 2012/0330349 | A1 * | 12/2012 | Jones ............... A61B 17/12109 606/200 |
| 2013/0066360 | A1 | 3/2013 | Becking et al. |
| 2013/0072961 | A1 | 3/2013 | Cage et al. |
| 2013/0085520 | A1 | 4/2013 | Liang et al. |
| 2013/0085522 | A1 | 4/2013 | Becking et al. |
| 2013/0152941 | A1 | 6/2013 | Nguyen et al. |
| 2013/0253572 | A1 | 9/2013 | Molaei et al. |
| 2013/0261730 | A1 | 10/2013 | Bose et al. |
| 2013/0296917 | A1 | 11/2013 | Rees |
| 2013/0331882 | A1 | 12/2013 | Tompkins et al. |
| 2014/0058434 | A1 | 2/2014 | Jones et al. |
| 2014/0058435 | A1 | 2/2014 | Jones et al. |
| 2014/0128907 | A1 | 5/2014 | Hui et al. |
| 2014/0135810 | A1 | 5/2014 | Divino et al. |
| 2014/0135811 | A1 | 5/2014 | Divino et al. |
| 2014/0135812 | A1 | 5/2014 | Divino et al. |
| 2014/0135818 | A1 | 5/2014 | Gandhi et al. |
| 2014/0148843 | A1 | 5/2014 | Strauss et al. |
| 2014/0172001 | A1 | 6/2014 | Becking et al. |
| 2014/0236127 | A1 | 8/2014 | Lee et al. |
| 2014/0236217 | A1 | 8/2014 | Gandhi et al. |
| 2014/0330299 | A1 | 11/2014 | Rosenbluth et al. |
| 2014/0358175 | A1 | 12/2014 | Tompkins et al. |
| 2015/0005807 | A1 | 1/2015 | Lagodzki et al. |
| 2015/0066073 | A1 * | 3/2015 | Ma ..................... A61B 17/1214 606/200 |
| 2015/0073524 | A1 | 3/2015 | Bennett et al. |
| 2015/0112378 | A1 | 4/2015 | Torp |
| 2015/0157332 | A1 | 6/2015 | Obermiller et al. |
| 2015/0173772 | A1 | 6/2015 | Bowman et al. |
| 2015/0196304 | A1 | 7/2015 | Rabkin et al. |
| 2015/0196355 | A1 | 7/2015 | Guimaraes |
| 2015/0230802 | A1 | 8/2015 | Lagodzki et al. |
| 2015/0257763 | A1 | 9/2015 | Blum et al. |
| 2015/0272589 | A1 | 10/2015 | Lorenzo |
| 2015/0297240 | A1 | 10/2015 | Divino et al. |
| 2015/0327868 | A1 | 11/2015 | Islak et al. |
| 2015/0335333 | A1 | 11/2015 | Jones et al. |
| 2015/0342611 | A1 | 12/2015 | Leopold et al. |

(56) References Cited

U.S. PATENT DOCUMENTS

| | | |
|---|---|---|
| 2015/0343181 A1 | 12/2015 | Bradway et al. |
| 2016/0008003 A1 | 1/2016 | Kleshinski et al. |
| 2016/0022270 A1 | 1/2016 | Watson et al. |
| 2016/0022445 A1 | 1/2016 | Ruvalcaba et al. |
| 2016/0030052 A1 | 2/2016 | Cragg et al. |
| 2016/0166257 A1 | 6/2016 | Allen et al. |
| 2016/0192942 A1 | 7/2016 | Strauss et al. |
| 2016/0228123 A1 | 8/2016 | Anderson et al. |
| 2016/0228124 A1 | 8/2016 | Trommeter et al. |
| 2016/0228128 A1 | 8/2016 | Connolly |
| 2016/0228287 A1 | 8/2016 | Shadduck et al. |
| 2016/0249934 A1 * | 9/2016 | Hewitt ............. A61B 17/12177 606/200 |
| 2016/0270846 A1 | 9/2016 | Truckai et al. |
| 2016/0317156 A1 | 11/2016 | Fitz et al. |
| 2016/0317274 A1 | 11/2016 | Liu et al. |
| 2017/0007261 A1 * | 1/2017 | Paamand ......... A61B 17/12113 |
| 2017/0100126 A1 | 4/2017 | Bowman et al. |
| 2017/0143349 A1 | 5/2017 | Raabe et al. |

FOREIGN PATENT DOCUMENTS

| | | |
|---|---|---|
| JP | 2016537134 A | 12/2016 |
| WO | 0232496 A1 | 4/2002 |
| WO | 2007047111 A1 | 4/2007 |
| WO | 2007070797 A2 | 6/2007 |
| WO | 2010030993 A1 | 3/2010 |
| WO | 2014145005 A3 | 4/2015 |

OTHER PUBLICATIONS

PCT Application No. PCT/US2017/061779 International Search Report and Written Opinion, dated Feb. 26, 2018.

International Search Report and Written Opinion dated Jul. 13, 2018 for International Application No. PCT/US2018/028240.

* cited by examiner

DETACHABLE RF ENERGIZED OCCLUSIVE DEVICE

CROSS-REFERENCE TO RELATED APPLICATIONS

This application claims the benefit of priority under 35 U.S.C. § 119 to U.S. Provisional Application Ser. No. 62/570,173, filed Oct. 10, 2017, the entirety of which is incorporated herein by reference.

TECHNICAL FIELD

The present disclosure pertains to medical devices and methods for manufacturing and/or using medical devices. More particularly, the present disclosure pertains to configurations of an occlusive medical device.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, an occlusive medical device system may comprise a microcatheter having a lumen extending from a proximal end of the microcatheter to a distal end of the microcatheter; an elongate shaft slidably disposed within the lumen of the microcatheter, the elongate shaft having a lumen extending from a proximal end of the elongate shaft to a distal end of the elongate shaft; an occlusive medical device disposed proximate the distal end of the elongate shaft, wherein the occlusive medical device is releasably attached to the distal end of the elongate shaft at a release mechanism; and an RF generator electrically connected to the occlusive medical device through the release mechanism. In a first electrical state electrical current is not flowing to the occlusive medical device, and in a second electrical state electrical current is flowing to the occlusive medical device. The elongate shaft is slidable between a first position wherein the occlusive medical device is disposed within the lumen of the microcatheter, a second position wherein at least a portion of the occlusive medical device is disposed outside of the lumen of the microcatheter and the release mechanism is disposed within the lumen of the microcatheter, and a third position wherein the release mechanism is disposed outside of the lumen of the microcatheter. The occlusive medical device system is configured to be in the second electrical state when the elongate shaft is in the second position.

In addition or alternatively, and in a second aspect, a release wire may be slidably disposed within the lumen of the elongate shaft. The release wire may be configured to releasably attach the occlusive medical device to the distal end of the elongate shaft at the release mechanism when the release wire extends through the release mechanism into the occlusive medical device. The RF generator may be electrically connected to the occlusive medical device by the release wire.

In addition or alternatively, and in a third aspect, the release wire comprises a nitinol composite wire having an electrically-conductive element.

In addition or alternatively, and in a fourth aspect, the release wire includes a nitinol wire having a core which is more electrically conductive than the nitinol wire.

In addition or alternatively, and in a fifth aspect, the release wire includes a nitinol core with a metal coating which is more electrically conductive than the nitinol core.

In addition or alternatively, and in a sixth aspect, proximal withdrawal of the release wire from the release mechanism when the elongate shaft is in the third position releases the occlusive medical device from the elongate shaft.

In addition or alternatively, and in a seventh aspect, the elongate shaft includes a first portion of the release mechanism attached to the distal end of the elongate shaft and the occlusive medical device includes a second portion of the release mechanism attached to a proximal end of the occlusive medical device.

In addition or alternatively, and in an eighth aspect, the release wire interlocks the first portion of the release mechanism with the second portion of the release mechanism when the release wire extends through the release mechanism such that relative axial translation between the first portion of the release mechanism and the second portion of the release mechanism is prevented.

In addition or alternatively, and in a ninth aspect, the occlusive medical device system is configured to be in the second electrical state when the elongate shaft is in the second position only.

In addition or alternatively, and in a tenth aspect, an occlusive medical device system may comprise a microcatheter having a lumen extending from a proximal end of the microcatheter to a distal end of the microcatheter; an elongate shaft slidably disposed within the lumen of the microcatheter, the elongate shaft having a lumen extending from a proximal end of the elongate shaft to a distal end of the elongate shaft; an occlusive medical device disposed proximate the distal end of the elongate shaft; a release wire slidably disposed within the lumen of the elongate shaft, wherein the release wire is configured to releasably attach an occlusive medical device to the distal end of the elongate shaft at a release mechanism when the release wire extends through the release mechanism into the occlusive medical device; and an RF generator electrically connected to the occlusive medical device, wherein the elongate shaft is non-conductive and the release wire is conductive. In a first electrical state electrical current is not flowing to the occlusive medical device, and in a second electrical state electrical current is flowing to the occlusive medical device. The elongate shaft is slidable between a first position wherein the occlusive medical device is disposed within the lumen of the microcatheter, a second position wherein at least a portion of the occlusive medical device is disposed outside of the lumen of the microcatheter and the release mechanism is disposed within the lumen of the microcatheter, and a third position wherein the release mechanism is disposed outside of the lumen of the microcatheter. The occlusive medical device system is configured to be in the second electrical state when the elongate shaft is in the second position.

In addition or alternatively, and in an eleventh aspect, the occlusive medical device comprises a metallic coiled member.

In addition or alternatively, and in a twelfth aspect, the metallic coiled member includes platinum.

In addition or alternatively, and in a thirteenth aspect, the metallic coiled member includes gold plating.

In addition or alternatively, and in a fourteenth aspect, in the second electrical state, electrical current flowing to the occlusive medical device causes resistance heating of the occlusive medical device.

In addition or alternatively, and in a fifteenth aspect, the occlusive medical device is configured to assume a first shape when disposed within the lumen of the microcatheter and a second shape when disposed outside of the lumen of the microcatheter.

In addition or alternatively, and in a sixteenth aspect, a method of promoting embolization within a body lumen may comprise: advancing a microcatheter to a treatment site within the body lumen, the microcatheter having an occlusive medical device disposed at a distal end of an elongate shaft slidably disposed within a lumen of the microcatheter proximate a distal end of the microcatheter; advancing the occlusive medical device out of the distal end of the microcatheter until a release mechanism securing the occlusive medical device to the distal end of the elongate shaft is disposed proximate the distal end of the microcatheter; sending RF energy to the occlusive medical device while the release mechanism is disposed within the distal end of the microcatheter and at least a portion of the occlusive medical device is disposed outside of the microcatheter to heat the treatment site causing stricture or size reduction of the body lumen and coagulation of blood around the occlusive medical device; and detaching the occlusive medical device from the elongate shaft at the release mechanism.

In addition or alternatively, and in a seventeenth aspect, when the occlusive medical device is detached from the elongate shaft at the release mechanism, the release mechanism is free from coagulation thereon.

In addition or alternatively, and in an eighteenth aspect, the release mechanism comprises a first portion attached to the distal end of the elongate shaft and a second portion attached to a proximal end of the occlusive medical device. An interface between the first portion and the second portion remains free of coagulation thereon until the occlusive medical device is detached from the elongate shaft.

In addition or alternatively, and in a nineteenth aspect, detaching the occlusive medical device from the elongate shaft includes slidably retracting a release wire extending through the release mechanism and at least partially into the occlusive medical device.

In addition or alternatively, and in a twentieth aspect, sending RF energy to the occlusive medical device occurs for less than 5 minutes.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
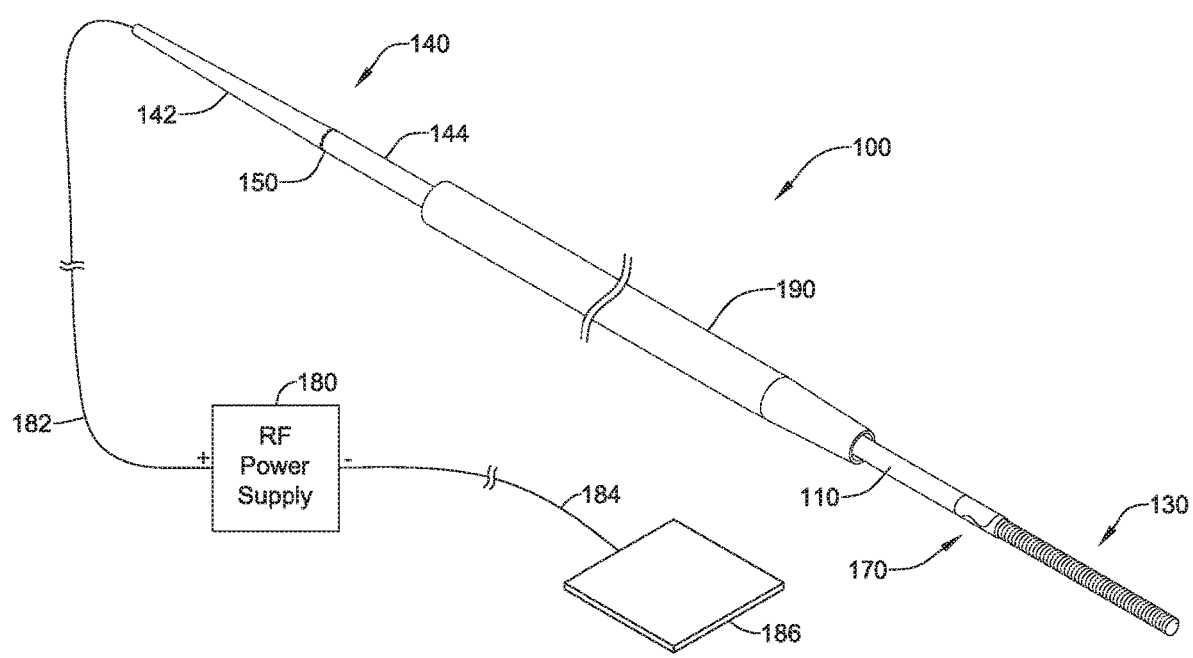
FIG. 1 is a perspective view of an occlusive medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to correspond to a measurement of a stated of identified dimension. The term "maximum extent" may be understood to mean a greatest measurement of a stated or identified dimension, while the term "minimum extent" may be understood to mean a smallest measurement of a stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, a "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 2:
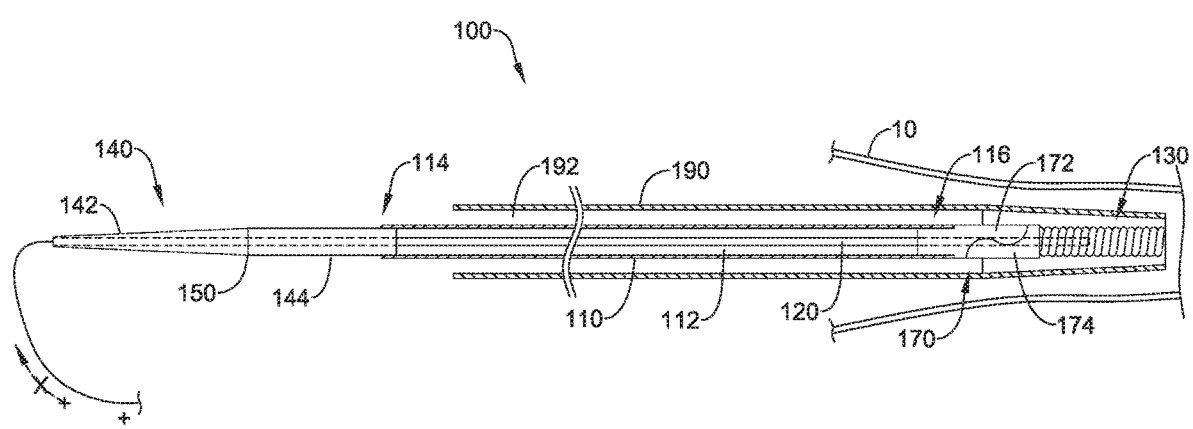
FIGS. 2-4 are partial cut-away views illustrating an example method of promoting embolization in accordance with the disclosure.

FIG. 1 illustrates aspects of an example occlusive medical device system 100, some additional aspects of which may be seen in, and are described with respect to, the partial cut-away view of FIG. 2. The occlusive medical device system 100 may include an elongate shaft 110 having a lumen 112 extending from a proximal end 114 of the elongate shaft 110 to a distal end 116 of the elongate shaft 110. In some embodiments, the elongate shaft 110 may be a catheter, a hypotube, or other similar tubular structure. In at least some embodiments, the elongate shaft 110 may be non-conductive and/or may be formed from a substantially non-conductive material. Alternatively, in some embodiment, the elongate shaft 110 may be conductive, maybe formed from a conductive mated al, and/or may include one or more conductive elements. Combinations of these configurations are also contemplated. Some suitable but non-limiting materials for the elongate shaft 110, for example metallic materials, polymer materials, composite materials, etc., are described below.

An occlusive medical device 130 may be disposed proximate the distal end 116 of the elongate shaft 110 and may be releasably attached thereto by a release mechanism 170. In some embodiments, the occlusive medical device 130 may be a metallic coiled member. For simplicity, the occlusive medical device 130 is illustrated herein as a shape memory embolic coil, such as those used to treat aneurysms for example, but other suitable medical devices transported, delivered, used, released etc. in a similar manner are also contemplated, including but not limited to stents, embolic filters, replacement heart valves, occlusion devices, and/or other medical implants, etc. In some embodiments, the occlusive medical device 130, the metallic coiled member, etc. may include a biocompatible and/or electrically conductive material. In some embodiments, the occlusive medical device 130 may have an outer diameter or maximum outer extent measured radially and/or laterally from a central longitudinal axis of the elongate shaft 110 of 20 mm or less, 15 mm or less, 10 mm or less, 8 mm or less, 6 mm or less, 5 mm or less, 3 mm or less, 2 mm or less, 1 mm or less, or another suitable size for the intended purpose. In some embodiments, the occlusive medical device 130, the metallic coiled member, etc. may include and/or be formed from platinum, gold, or other suitable precious metals, etc. and/or may include a platinum coating, a gold coating, or other suitable coating. Some suitable but non-limiting materials for the occlusive medical device 130, for example metallic materials, composite materials, electrically-conductive materials, etc., are described below.

In some embodiments, the occlusive medical device system 100 may include an RF power supply and/or generator 180 electrically connected to the occlusive medical device 130. In some embodiments, the occlusive medical device system 100 may include a first lead 182 electrically connecting the RF power supply and/or generator 180 to a release wire 120 (e.g., FIG. 2), described further below, and a second lead 184 electrically connecting the RF power supply and/or generator 180 to a reference pad 186. The reference pad 186 may be adapted and configured for placement on a patient's skin to provide a conductive pathway for monopolar current flow from the RF power supply and/or generator 180, through the first lead 182 and the release wire 120 to the occlusive medical device 130, as will be described in more detail below. Current may flow through the patient (e.g., a vessel wall and/or tissue, surrounding tissue(s), etc.) to the reference pad 186 on the patient's skin and back to the RF power supply and/or generator 180. In some embodiments, the reference pad 186 may be omitted and a bipolar current design electrically connecting both the first lead 182 and the second lead 184 through the release wire 120 and/or the elongate shaft 110 to the occlusive medical device 130 may be utilized. The occlusive medical device system 100 and/or the RF power supply and/or generator 180 may define a first electrical state and a second electrical state, wherein in the first electrical state electrical current (e.g., RF energy) is not flowing to the occlusive medical device 130, and wherein in the second electrical state electrical current (e.g., RF energy) is flowing to the occlusive medical device 130.

As best seen in FIG. 2, the occlusive medical device system 100 may include a release wire 120 slidably disposed within the lumen 112 of the elongate shaft 110. The release wire 120 may be configured to releasably attach the occlusive medical device 130 to the distal end 116 of the elongate shaft 110 at the release mechanism 170 when the release wire 120 extends through the release mechanism 170 into the occlusive medical device 130. The release mechanism 170 may form a joint, and may include a first portion 172 and a second portion 174. The release mechanism 170 and/or the joint will be described in more detail below. In some embodiments, the release wire 120 may be alternately and/or interchangeably referred to as a pull wire, an actuation wire, and/or a locking wire. In some embodiments, the RF power supply and/or generator 180 may be electrically connected to the occlusive medical device 130 by the release wire 120. The release wire 120 may generally be a solid wire or shaft, but may also be tubular in some embodiments. In some embodiments, the release wire 120 may be a composite wire comprising more than one discrete material (e.g., two discrete materials, three discrete materials, etc.). For example, in some embodiments, the release wire 120 may comprise a nitinol, superelastic, and/or shape memory wire having an electrically conductive element, as described further below. At least a portion of the release wire 120 and/or the electrically conductive element proximate a distal end of the release wire 120 may be in direct contact with and/or in electrical communication with the occlusive medical device 130. Some suitable but non-limiting materials for the release wire 120, for example metallic materials, polymer materials, composite materials, etc., are described below.

In some embodiments, the occlusive medical device system 100 may include a microcatheter 190 sized and configured to deliver the occlusive medical device 130 to a treatment site within a body lumen 10 (e.g., FIG. 2). The elongate shaft 110 and the occlusive medical device 130 may be slidably disposed within a lumen 192 of the microcatheter 190, the lumen 192 of the microcatheter 190 extending from a proximal end of the microcatheter 190 to a distal end of the microcatheter 190. In some embodiments, the microcatheter 190 may facilitate percutaneous delivery of the occlusive medical device 130 to the treatment site within the body lumen 10. Some suitable but non-limiting materials for the microcatheter 190, for example metallic materials, polymer materials, composite materials, etc., are described below.

In an alternative configuration, the occlusive medical device 130 may be releasably attached to the elongate shaft 110 at the release mechanism 170 and/or the joint when the release mechanism 170 and/or the joint is disposed within the lumen 192 of the microcatheter 190. For example, the microcatheter 190 may provide and/or impose a mechanical interlock upon the first portion 172 and the second portion 174 of the release mechanism 170 and/or the joint, thereby preventing the occlusive medical device 130 from detaching from the elongate shaft 110 when the elongate shaft 110 is in the first position and/or the second position. In such a configuration, the release wire 120 may be optional and/or may not be strictly necessary for operation of the occlusive medical device system 100. When the elongate shaft 110 is in the third position, and/or when the release mechanism 170 and/or the joint is advanced out of and/or relative to the microcatheter 190, the microcatheter 190 no longer maintains the mechanical interlock and the occlusive medical device 130 may be released. In some embodiments, the RF power supply and/or generator 180 may be electrically connected to the occlusive medical device 130 by the elongate shaft 110 and/or a separate electrical conductor extending along the elongate shaft 110.

In another alternative embodiment, the first portion 172 of the release mechanism 170 and/or the joint may include jaws configured to grasp the second portion 174 of the release mechanism 170, the joint, and/or a proximal end of the occlusive medical device 130. The first portion 172 and/or the jaws may electrically connect the RF power supply and/or generator 180 to the occlusive medical device 130. In some embodiments, the release mechanism 170 and/or the joint may include an electrolytic element and the jaws may grasp and/or attach to the electrolytic element. In some embodiments, the release mechanism 170 and/or the joint may further include a tether between the first portion 172 and the second portion 174. When RF energy and/or electrical current is sent to the occlusive medical device 130 as described in more detail below, the RF energy and/or electrical current may be transmitted through the electrolytic element to the occlusive medical device 130. When it is desired to release the occlusive medical device 130, and/or after a predetermined period of time has passed, the electrolytic element may break, dissolve, and/or be configured to fail when an increased RF energy or electrical current is applied. For example, the electrolytic element may transmit RF energy or electrical current up to a desired current level either indefinitely until an increased amount of RF energy or electrical current is sent and/or applied to cause the electrolytic element to fail, or for a predetermined period of time, at which point the electrolytic may automatically fail, thereby breaking the electrical connection.

In some embodiments, the occlusive medical device system 100 may include a securement member 140 fixedly attached to and/or extending proximally from the proximal end 114 of the elongate shaft 110, and fixedly attached to a proximal end of the release wire 120. The release wire 120 may extend through at least a portion of the securement member 140. The securement member 140 may include a proximal portion 142 and a distal portion 144 attached to the proximal portion 142. In at least some embodiments, the proximal portion 142 of the securement member 140 may be integrally formed with the distal portion 144 of the securement member 140 as a single unitary structure. Some suitable but non-limiting materials for the securement member 140, for example metallic materials, polymer materials, composite materials, etc., are described below.

In some embodiments, the proximal portion 142 of the securement member 140 may be configured to disengage from the distal portion 144 of the securement member 140. In some embodiments, the proximal portion 142 of the securement member 140 may be fixedly attached to the proximal end of the release wire 120. The distal portion 144 of the securement member 140 may be fixedly attached to the proximal end 114 of the elongate shaft 110. In at least some embodiments, an outer surface of the distal portion 144 of the securement member 140 may be fixedly attached to an inner surface of the elongate shaft 110 (e.g., a surface defining the lumen 112). Alternatively, in some embodiments, an inner surface of the distal portion 144 of the securement member 140 may be fixedly attached to an outer surface of the elongate shaft 110. In some embodiments, the proximal portion 142 of the securement member 140 may be releasably secured to and/or configured to disengage from the distal portion 144 of the securement member 140 at a perforation and/or a frangible link 150 formed in a wall of the securement member 140.

In at least some embodiments, the securement member 140 may prevent axial translation of the release wire 120 relative to the elongate shaft 110 and/or the occlusive medical device 130 prior to disengagement of the proximal portion 142 of the securement member 140 from the distal portion 144 of the securement member 140. Disengaging the proximal portion 142 of the securement member 140 from the distal portion 144 of the securement member 140 may permit the release wire 120 to axially translate relative to the distal portion 144 of the securement member 140 and/or the elongate shaft 110. In some embodiments, the wall of the distal portion 144 of the securement member 140 may define a lumen, wherein the release wire 120 is slidably disposed within the lumen of the distal portion 144 of the securement member 140. Upon disengagement of the proximal portion 142 of the securement member 140 from the distal portion 144 of the securement member 140, axial translation of the proximal portion 142 relative to the distal portion 144 of the securement member 140 and/or the elongate shaft 110 may translate the release wire 120 relative to the elongate shaft 110 and/or the distal portion 144 of the securement member 140 to release the occlusive medical device 130 from the distal end 116 of the elongate shaft 110, as will be explained in more detail herein.

In use, for example in a method of promoting embolization within the body lumen 10, the microcatheter 190 of the occlusive medical device system 100 may be inserted into a patient's anatomy and a distal end guided and/or advanced to a location adjacent a treatment site within the body lumen 10, as seen in FIG. 2 for example. The occlusive medical device 130 disposed at the distal end 116 of the elongate shaft 110 may be inserted into a proximal end of the lumen 192 disposed within the microcatheter 190 and advanced through the microcatheter 190 to the treatment site. In some embodiments, the occlusive medical device 130 may be disposed within the lumen 192 of the microcatheter 190 proximate to the distal end 116 of the elongate shaft 110. In some embodiments, the occlusive medical device 130 may be disposed within the lumen 192 of the microcatheter 190 proximate to the distal end 116 of the elongate shaft 110 prior to use and/or prior to inserting the microcatheter 190 into the patient's anatomy and/or advancing the distal end to the location adjacent the treatment site within the body lumen 10.

In some embodiments, the elongate shaft 110 may be slidable between a first position (e.g., FIG. 2) wherein the occlusive medical device 130 is disposed within the lumen 192 of the microcatheter 190, a second position (e.g., FIG. 3) wherein at least a portion of the occlusive medical device 130 is disposed outside of the lumen 192 of the microcatheter 190 and the release mechanism 170 and/or the joint is disposed within the lumen 192 of the microcatheter 190, and a third position (e.g., FIG. 4) wherein the release mechanism 170 and/or the joint (and the occlusive medical device 130) is disposed outside of the lumen 192 of the microcatheter 190. In at least one example, the occlusive medical device system 100 is configured to be in the first electrical state when the elongate shaft 110 is disposed in the first position, such that electrical current (e.g., RF energy) is not flowing to the occlusive medical device 130, as shown in FIG. 2 for example. Since the electrical current may heat the occlusive medical device 130 and/or any surrounding blood within the body lumen 10, the electrical current may initiate, promote, and/or enhance coagulation of blood around the occlusive medical device 130. Accordingly, it is undesirable to initiate the flow of the electrical current while a majority (or all) of the occlusive medical device 130 is disposed within the lumen 192 of the microcatheter 190 (e.g., when the elongate shaft 110 is disposed in the first position and/or when the elongate shaft 110 is between the first position and the second position).

Figure 3:
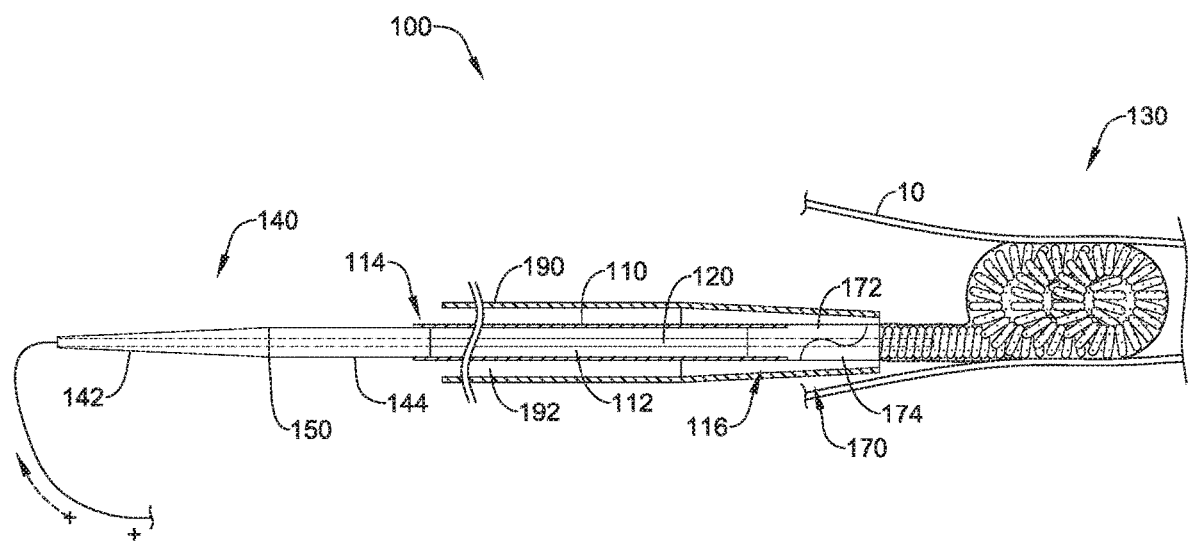

As shown in FIG. 3, after advancing the distal end of the microcatheter 190 to the treatment site within the body lumen 10, the method may include advancing the occlusive medical device 130 out of the distal end of the microcatheter 190 and/or axially translating the elongate shaft 110 and the microcatheter 190 relative to each other until the release mechanism 170 and/or the joint securing the occlusive medical device 130 to the distal end of the elongate shaft 110 is disposed proximate the distal end of the microcatheter 190 such that the elongate shaft 110 is in the second position. In some embodiments, the elongate shaft 110, the release mechanism 170 and/or the joint, and/or the occlusive medical device 130 may include an indicator (e.g., a mechanical indicator, a fluoroscopic indicator, etc.) for identifying that the elongate shaft HO is in and/or has reached the second position. In some embodiments, the occlusive medical device 130 may be formed from a shape memory material and/or may be biased to assume and/or return to a predetermined shape in an unstressed configuration outside of the lumen 192 of the microcatheter 190. For example, the occlusive medical device 130 may be configured to assume a first shape when disposed within the lumen 192 of the microcatheter 190 (e.g., FIG. 2), and a second shape different from the first shape when disposed outside of the lumen 192 of the microcatheter 190 (e.g., FIG. 3).

In some embodiments, the occlusive medical device 130 may be substantially flexible and/or deformable, when in the first shape, in the second shape, and/or in both the first shape and the second shape. For example, the occlusive medical device 130 may be configured to be packed into the body lumen 10 at the treatment site to substantially occlude the body lumen 10 by filling available space therein. While it is desirable to avoid initiating the flow of the electrical current while a majority (or all) of the occlusive medical device 130 is disposed within the lumen 192 of the microcatheter 190, it is also desirable to avoid and/or prevent coagulation from forming on and/or around the release mechanism 170 and/or the joint to facilitate detachment of the occlusive medical device 130 from the distal end 116 of the elongate shaft 110. In at least some embodiments, the occlusive medical device system 100 may be configured to be in the second electrical state when the elongate shaft 110 is in the second position, such that electrical current (e.g., RF energy) is flowing to the occlusive medical device 130, as shown in FIG. 3 for example. In some embodiments, the occlusive medical device system 100 may be configured to be in the second electrical state when the elongate shaft 110 is in the second position only.

In some embodiments, the method may include sending RF energy and/or electrical current to the occlusive medical device 130 while the release mechanism 170 and/or the joint is disposed within the distal end of the microcatheter 190 and at least a portion of the occlusive medical device 130 (and in some cases, all of the occlusive medical device 130) is disposed outside of the microcatheter 190 to heat the treatment site, the occlusive medical device 130, and/or any surrounding blood within the body lumen 10 causing stricture or size reduction of the body lumen 10 and coagulation of blood around the occlusive medical device 130. In some embodiments, when the occlusive medical device system 100 is in the second electrical state, electrical current (e.g., RF energy) flowing to the occlusive medical device 130 may cause resistance heating of the occlusive medical device 130. In some embodiments, sending RF energy and/or electrical current to the occlusive medical device 130 may occur for 5 minutes or less at a power level of 10 watts or less. In some embodiments, sending RF energy and/or electrical current to the occlusive medical device 130 may occur for 2 minutes or less at a power level of 10 watts or less. In some embodiments, sending RF energy and/or electrical current to the occlusive medical device 130 may occur for 10 minutes or less, 5 minutes or less, 3 minutes or less, 2 minutes or less, 1.5 minutes or less, 1 minute or less, 45 seconds or less, 30 seconds or less, 15 seconds or less, 10 seconds or less, and/or other suitable time intervals. In some embodiments, sending RF energy and/or electrical current to the occlusive medical device may occur at a power level of 100 watts or less, 75 watts or less, 50 watts or less, 25 watts or less, 15 watts or less, 7.5 watts or less, 5 watts or less, 3 watts or less, 2 watts or less, 1 watt or less, and/or other suitable power levels. Other combinations and/or variations of time interval and power level are also contemplated, wherein the time interval and/or power level may be selected to cause limited injury or trauma to the treatment site and/or a wall of the body lumen 10 to initiate bleeding, coagulation, and/or to provide an interface for clotting/coagulation to attach to the wall of the body lumen 10 without permanently damaging tissue or causing patient discomfort.

Figure 4:
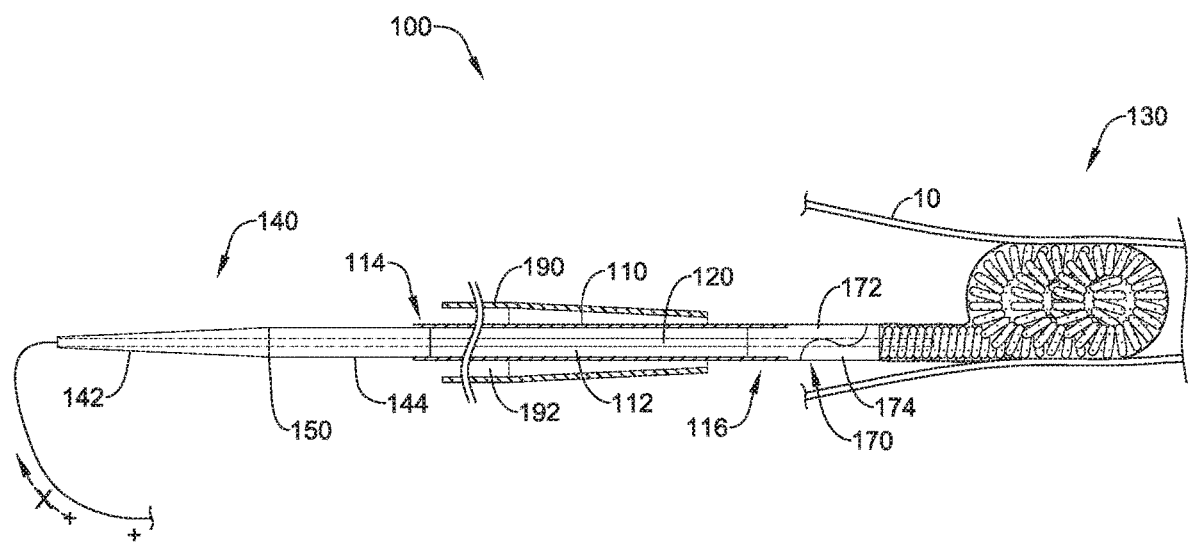

In some embodiments, after initiating the coagulation of blood and/or coagulating blood to a desired degree around the occlusive medical device 130 at the treatment site within the body lumen 10, the RF energy and/or flow of electrical current may be terminated. As shown in FIG. 4, in some embodiments, after initiating the coagulation of blood and/or coagulating blood to a desired degree around the occlusive medical device 130 at the treatment site within the body lumen 10, the microcatheter 190 may be withdrawn proximally and/or axially translated away from the occlusive medical device 130 such that the elongate shaft 110 is disposed in the third position wherein the release mechanism 170 and/or the joint is disposed outside of the lumen 192 of the microcatheter 190 at the treatment site. In at least one example, the occlusive medical device system 100 is configured to be in the first electrical state when the elongate shaft 110 is disposed in the third position, such that electrical current (e.g., RF energy) is not flowing to the occlusive medical device 130 when the release mechanism 170 and/or the joint is disposed outside of the lumen 192 of the microcatheter 190 at the treatment site, as shown in FIG. 4 for example.

Figure 5:
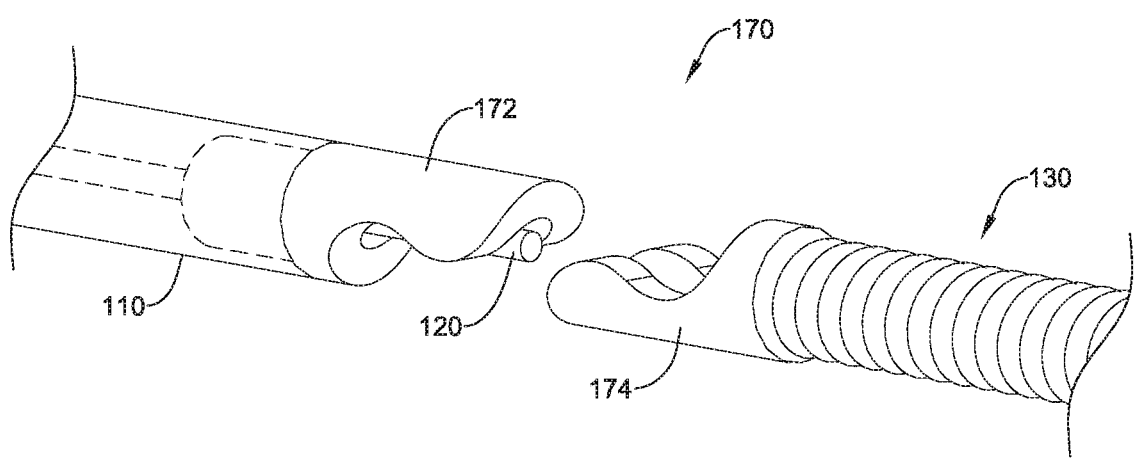
FIG. 5 illustrates an example joint and/or release mechanism of the occlusive medical device system.

In at least some embodiments, the release mechanism 170 may form a joint, and may include a first portion 172 and a second portion 174, wherein the elongate shaft 110 may include the first portion 172 of the release mechanism 170 and/or the joint fixedly attached to the distal end 116 of the elongate shaft 110 and the occlusive medical device 130 may include the second portion 174 of the release mechanism 170 and/or the joint fixedly attached to a proximal end of the occlusive medical device 130, as seen in FIG. 5 for example. A distal end of the release wire 120 may slidably engage with the first portion 172 of the release mechanism 170 and/or the joint and the second portion 174 of the release mechanism 170 and/or the joint. The release wire 120 interlocks the first portion 172 of the release mechanism 170 and/or the joint with the second portion 174 of the release mechanism 170 and/or the joint when the proximal portion 142 of the securement member 140 is engaged with the distal portion 144 of the securement member 140. Some suitable but non-limiting materials for the release mechanism 170 and/or the joint, for example metallic materials, polymer materials, composite materials, etc., are described below.

Figure 6:
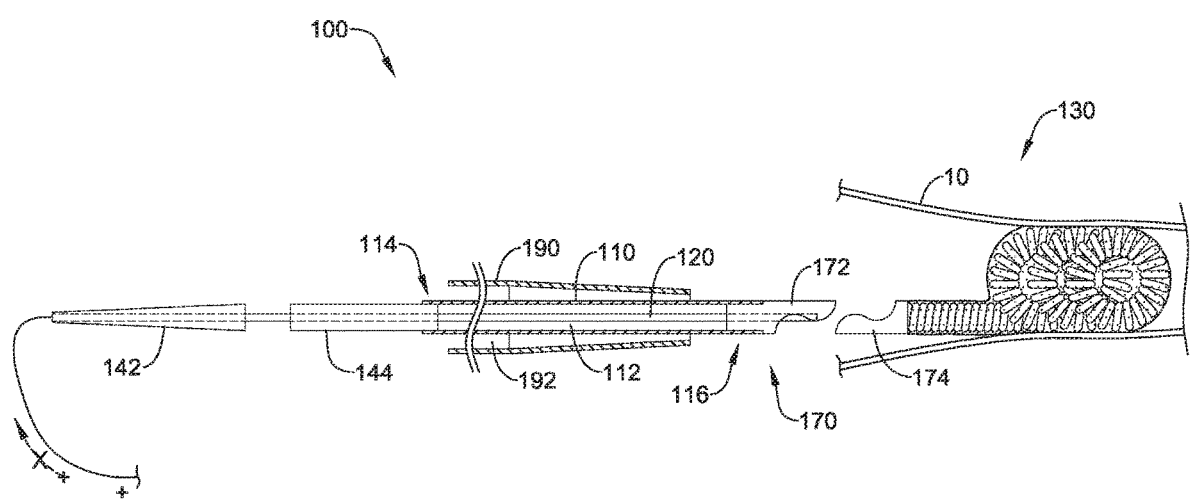
FIG. 6 is a partial cut-away view illustrating the release of an occlusive medical device.

In some embodiments, the method may include detaching the occlusive medical device 130 from the distal end 116 of the elongate shaft 110 at the release mechanism 170 and/or the joint. Proximal withdrawal of the release wire 120 from the release mechanism 170 and/or the joint when the elongate shaft 110 is in the third position may release the occlusive medical device 130 from the elongate shaft 110. For example, when the proximal portion 142 of the securement member 140 is disengaged and/or separated from the distal portion 144 of the securement member 140, as seen in FIG. 6, the release wire 120 is translated in a proximal direction relative to the elongate shaft 110 to release the second portion 174 of the release mechanism and/or the occlusive medical device 130 from the first portion 172 of the release mechanism and/or the elongate shaft 110. In at least some embodiments, the release wire 120 may be slidably disposed within the distal portion 144 of the securement member 140, the elongate shaft 110, the first portion 172 of the release mechanism, and the second portion 174 of the release mechanism. In some embodiments, detaching the occlusive medical device 130 from the distal end 116 of the elongate shaft 110 at the release mechanism 170 and/or the joint may include slidably retracting the release wire 120 extending through the release mechanism 170 and/or the joint and at least partially into the occlusive medical device 130.

In some embodiments, when the occlusive medical device 130 is detached from the distal end 116 of the elongate shaft 110 at the release mechanism 170 and/or the joint, the release mechanism 170 and/or the joint may be free from coagulation thereon. In some embodiments, an interface between the first portion 172 of the release mechanism and the second portion 174 of the release mechanism may remain free of coagulation thereon until the occlusive medical device 130 is detached from the distal end 116 of the elongate shaft 110.

Figure 7A:
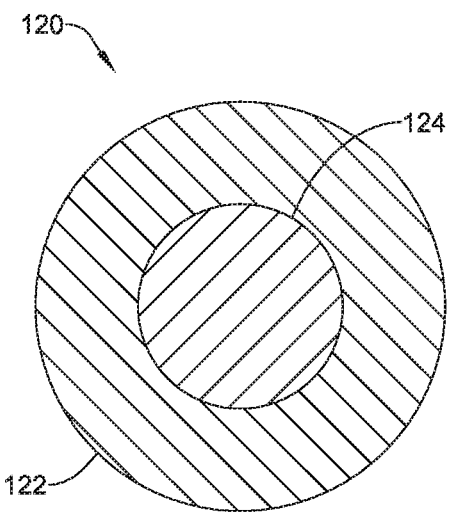
FIGS. 7A-7B are cross-sectional views illustrating example configurations of a release wire of the occlusive medical device system.
Figure 7B:
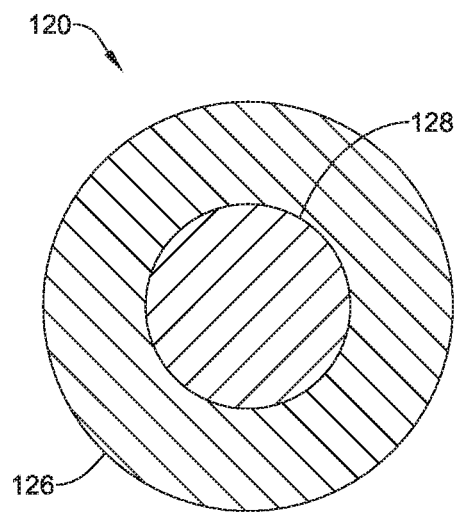

FIGS. 7A and 7B are cross-sectional views illustrating example configurations of the release wire 120. For example, as discussed above, the release wire 120 may be a composite wire comprising more than one discrete material (e.g., two discrete materials, three discrete materials, etc.). In some embodiments, the release wire 120 may comprise a nitinol, superelastic, and/or shape memory wire having an electrically-conductive element. In some embodiments, the release wire 120 may include a nitinol wire 122 having a core 124 which is more electrically conductive than the nitinol wire 122, for example, a precious metal core, as shown in FIG. 7A. In some embodiments, the release wire 120 may include a nitinol core 128 with a metal coating or cladding 126 which is more electrically conductive than the nitinol core 128, for example, a precious metal coating or cladding, as shown in FIG. 7B. In some embodiments, the release wire 120 may include a plurality of electrically-conductive elements embedded within and/or disposed on a nitinol wire, wherein the plurality of electrically-conductive elements is electrically insulated from each other. The electrically-conductive element(s) (e.g., the more electrically conductive core and/or precious metal core 124, the more electrically conductive metal coating and/or the precious metal coating or cladding 126, etc.) may be in electrical communication with the RF power supply and/or generator 180, the first lead 182, and/or the occlusive medical device 130. Some suitable but non-limiting materials for the release mechanism and/or the electrically-conductive element(s), the core 124, the metal coating or cladding 126, etc., for example metallic materials, polymer materials, composite materials, etc., are described below.

Returning to FIG. 1, the elongate shaft 110 may have sufficient length that the proximal end 114 of the elongate shaft 110 and/or the securement member 140 remain proximal of (e.g., extend proximally from) the microcatheter 190 when the occlusive medical device 130 is disposed distal of the microcatheter 190. In use, the elongate shaft 110 may have sufficient length to reach from the treatment site within the body lumen 10 to a position outside of the patient where the occlusive medical device system 100 may be manipulated by an operator (e.g., clinician, physician, user, etc.). The operator of the occlusive medical device system 100 may then place a first hand on the distal portion 144 of the securement member 140 and a second hand on the proximal portion 142 of the securement member 140. The proximal portion 142 of the securement member 140 may be configured to disengage from the distal portion 144 of the securement member 140 at a location proximal of a proximal end of the microcatheter 190 when the occlusive medical device 130 is disposed distal of the microcatheter 190 and/or the elongate shaft 110 is in the second position.

In at least some embodiments, the proximal portion 142 of the securement member 140 may be disengaged from the distal portion 144 of the securement member 140 by bending, twisting, and/or pulling the proximal portion 142 of the securement member 140 relative to the distal portion 144 of the securement member 140 (e.g., at the perforation or frangible link 150). In some embodiments, disengaging the proximal portion 142 of the securement member 140 from the distal portion 144 of the securement member 140 may include moving the proximal portion 142 of the securement member 140 relative to the distal portion 144 of the securement member 140 to separate the proximal portion 142 of the securement member 140 from the distal portion 144 of the securement member 140 at the perforation or frangible link 150. In some embodiments, disengaging the proximal portion 142 of the securement member 140 from the distal portion 144 of the securement member 140 may include using an external device (e.g., a torque device, an external handle, etc.) to move the proximal portion 142 of the securement member 140 relative to the distal portion 144 of the securement member 140.

The perforation or frangible link 150 may be formed in the wall of the securement member 140. In at least some embodiments, the perforation or frangible link 150 may include a series of apertures extending through the wall of the securement member 140. In at least some embodiments, the perforation or frangible link 150 may include a thinned and/or weakened feature, or series of features, formed in the wall of the securement member 140 that is more susceptible to fracture and/or separation than the remainder of the wall. In some embodiments, the securement member 140 may include a perforation and a frangible link. For example, a perforation may be formed within a frangible link. In some embodiments, a portion of the circumference of the securement member 140 may include a perforation while a different portion of the circumference of the securement member 140 may include a frangible link. Other combinations and/or configuration are also contemplated.

In some embodiments, the perforation or frangible link 150 may extend circumferentially about an entire circumference of the wall of the securement member 140. In some embodiments, the perforation or frangible link 150 may extend partially and/or intermittently about the entire circumference of the wall of the securement member 140. Additionally, while the perforation or frangible link 150 may be generally oriented and/or positioned within a plane perpendicular to a longitudinal axis of the securement member 140, other orientations and/or positioning may be used. For example, in some embodiments, the perforation or frangible link 150 and/or the series of apertures may be oriented and/or positioned within or along a plane at an oblique angle to the longitudinal axis of the securement member 140. Other, for example non-planar, configurations are also possible. The proximal portion 142 of the securement member 140 is disposed proximal of the perforation or frangible link 150 and the distal portion 144 of the securement member 140 is disposed distal of the perforation or frangible link 150. As mentioned above, the proximal portion 142 of the securement member 140 may be releasably secured to and/or configured to disengage from the distal portion 144 of the securement member 140 at the perforation or frangible link 150 formed in the wall of the securement member 140.

The materials that can be used for the various components of the occlusive medical device system 100, the elongate shaft 110, the release wire 120, the occlusive medical device 130, the securement member 140, the release mechanism 170, and/or the microcatheter 190, etc. (and/or other systems disclosed herein) and the various elements thereof disclosed herein may include those commonly associated with medical devices. For simplicity purposes, the following discussion makes reference to the occlusive medical device system 100, the elongate shaft 110, the release wire 120, the occlusive medical device 130, the securement member 140, the release mechanism 170, and/or the microcatheter 190, etc. However, this is not intended to limit the devices and methods described herein, as the discussion may be applied to other elements, members, components, or devices disclosed herein, such as, but not limited to, the occlusive medical device system 100, the elongate shaft 110, the release wire 120, the occlusive medical device 130, the securement member 140, the release mechanism 170, and/or the microcatheter 190, etc. and/or elements or components thereof.

In some embodiments, the occlusive medical device system 100, the elongate shaft 110, the release wire 120, the occlusive medical device 130, the securement member 140, the release mechanism 170, and/or the microcatheter 190, etc., and/or components thereof and/or associated therewith (such as, but not limited to, the core 124, the metal coating 126, the proximal portion 142, the distal portion 144, the first portion 172, the second portion 174, the first lead 182, the second lead 184, the reference pad 186, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum, platinum iridium alloys, platinum enriched stainless steel, and/or other platinum alloys; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive medical device system 100, the elongate shaft 110, the release wire 120, the occlusive medical device 130, the securement member 140, the release mechanism 170, and/or the microcatheter 190, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive medical device system 100, the elongate shaft 110, the release wire 120, the occlusive medical device 130, the securement member 140, the release mechanism 170, and/or the microcatheter 190, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive medical device system 100, the elongate shaft 110, the release wire 120, the occlusive medical device 130, the securement member 140, the release mechanism 170, and/or the microcatheter 190, etc. to achieve the same result.

In some embodiments, a degree of Magnetic Resonance Imaging (MRI) compatibility is imparted into the occlusive medical device system 100, the elongate shaft 110, the release wire 120, the occlusive medical device 130, the securement member 140, the release mechanism 170, and/or the microcatheter 190, etc. For example, the occlusive medical device system 100, the elongate shaft 110, the release wire 120, the occlusive medical device 130, the securement member 140, the release mechanism 170, and/or the microcatheter 190, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive medical device system 100, the elongate shaft 110, the release wire 120, the occlusive medical device 130, the securement member 140, the release mechanism 170, and/or the microcatheter 190, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive medical device system 100, the elongate shaft 110, the release wire 120, the occlusive medical device 130, the securement member 140, the release mechanism 170, and/or the microcatheter 190, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylenelpoly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-h-isobutylene-h-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the occlusive medical device 130 and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An occlusive medical device system, comprising:
a microcatheter having a lumen extending from a proximal end of the microcatheter to a distal end of the microcatheter;
an elongate shaft slidably disposed within the lumen of the microcatheter, the elongate shaft having a lumen extending from a proximal end of the elongate shaft to a distal end of the elongate shaft;
an occlusive medical device disposed proximate the distal end of the elongate shaft, wherein the occlusive medical device is releasably attached to the distal end of the elongate shaft at a release mechanism; and
an RF generator electrically connected to the occlusive medical device through the release mechanism;
wherein in a first electrical state electrical current is not flowing to the occlusive medical device, and wherein in a second electrical state electrical current is flowing to the occlusive medical device;
wherein the elongate shaft is slidable between a first position wherein the occlusive medical device is disposed within the lumen of the microcatheter, a second position wherein at least a portion of the occlusive medical device is disposed outside of the lumen of the microcatheter and the release mechanism is disposed within the lumen of the microcatheter, and a third position wherein the release mechanism is disposed outside of the lumen of the microcatheter;
wherein the occlusive medical device system is configured to be in the second electrical state when the elongate shaft is in the second position, wherein a release wire is slidably disposed within the lumen of the elongate shaft, wherein the release wire is configured to releasably attach the occlusive medical device to the distal end of the elongate shaft at the release mechanism when the release wire extends through the release mechanism into the occlusive medical device.

2. The occlusive medical device system of claim 1, wherein the RF generator is electrically connected to the occlusive medical device by the release wire.

3. The occlusive medical device system of claim 2, wherein the release wire comprises a nitinol composite wire having an electrically-conductive element.

4. The occlusive medical device system of claim 3, wherein the release wire includes a nitinol wire having a core which is more electrically conductive than the nitinol wire.

5. The occlusive medical device system of claim 3, wherein the release wire includes a nitinol core with a metal coating which is more electrically conductive than the nitinol core.

6. The occlusive medical device system of claim 2, wherein proximal withdrawal of the release wire from the release mechanism when the elongate shaft is in the third position releases the occlusive medical device from the elongate shaft.

7. The occlusive medical device system of claim 2, wherein the elongate shaft includes a first portion of the release mechanism attached to the distal end of the elongate shaft and the occlusive medical device includes a second portion of the release mechanism attached to a proximal end of the occlusive medical device.

8. The occlusive medical device system of claim 7, wherein the release wire interlocks the first portion of the release mechanism with the second portion of the release mechanism when the release wire extends through the release mechanism such that relative axial translation between the first portion of the release mechanism and the second portion of the release mechanism is prevented.

9. The occlusive medical device system of claim 1, wherein the occlusive medical device system is configured to be in the second electrical state when the elongate shaft is in the second position only.

10. An occlusive medical device system, comprising:
a microcatheter having a lumen extending from a proximal end of the microcatheter to a distal end of the microcatheter;
an elongate shaft slidably disposed within the lumen of the microcatheter, the elongate shaft having a lumen extending from a proximal end of the elongate shaft to a distal end of the elongate shaft;
an occlusive medical device disposed proximate the distal end of the elongate shaft;
a release wire slidably disposed within the lumen of the elongate shaft, wherein the release wire is configured to releasably attach an occlusive medical device to the distal end of the elongate shaft at a release mechanism when the release wire extends through the release mechanism into the occlusive medical device; and
an RF generator electrically connected to the occlusive medical device through the release mechanism, wherein the elongate shaft is non-conductive and the release wire is conductive;
wherein in a first electrical state electrical current is not flowing to the occlusive medical device, and wherein in a second electrical state electrical current is flowing to the occlusive medical device;
wherein the elongate shaft is slidable between a first position wherein the occlusive medical device is disposed within the lumen of the microcatheter, a second position wherein at least a portion of the occlusive medical device is disposed outside of the lumen of the microcatheter and the release mechanism is disposed within the lumen of the microcatheter, and a third position wherein the release mechanism is disposed outside of the lumen of the microcatheter;
wherein the occlusive medical device system is configured to be in the second electrical state when the elongate shaft is in the second position, wherein a release wire is slidably disposed within the lumen of the elongate shaft, wherein the release wire is configured to releasably attach the occlusive medical device to the distal end of the elongate shaft at the release mechanism when the release wire extends through the release mechanism into the occlusive medical device.

11. The occlusive medical device system of claim 10, wherein the occlusive medical device comprises a metallic coiled member.

12. The occlusive medical device system of claim 11, wherein the metallic coiled member includes platinum.

13. The occlusive medical device system of claim 11, wherein the metallic coiled member includes gold plating.

14. The occlusive medical device system of claim 10, wherein in the second electrical state, electrical current flowing to the occlusive medical device causes resistance heating of the occlusive medical device.

15. The occlusive medical device system of claim 10, wherein the occlusive medical device is configured to assume a first shape when disposed within the lumen of the microcatheter and a second shape when disposed outside of the lumen of the microcatheter.

16. A method of promoting embolization within a body lumen, comprising:
advancing a microcatheter to a treatment site within the body lumen, the microcatheter having an occlusive medical device disposed at a distal end of an elongate shaft slidably disposed within a lumen of the microcatheter proximate a distal end of the microcatheter;
advancing the occlusive medical device out of the distal end of the microcatheter until a release mechanism securing the occlusive medical device to the distal end of the elongate shaft is disposed proximate the distal end of the microcatheter;
sending RF energy to the occlusive medical device through the release mechanism while the release mechanism is disposed within the distal end of the microcatheter and at least a portion of the occlusive medical device is disposed outside of the microcatheter to heat the treatment site causing stricture or size reduction of the body lumen and coagulation of blood around the occlusive medical device; and
detaching the occlusive medical device from the elongate shaft at the release mechanism, wherein detaching the occlusive medical device from the elongate shaft includes slidably retracting a release wire extending through the release mechanism and at least partially into the occlusive medical device.

17. The method of claim 16, wherein when the occlusive medical device is detached from the elongate shaft at the release mechanism, the release mechanism is free from coagulation thereon.

18. The method of claim 16, wherein the release mechanism comprises a first portion attached to the distal end of the elongate shaft and a second portion attached to a proximal end of the occlusive medical device;
wherein an interface between the first portion and the second portion remains free of coagulation thereon until the occlusive medical device is detached from the elongate shaft.

19. The method of claim 16, wherein sending RF energy to the occlusive medical device occurs for less than 5 minutes.

* * * * *